(12) United States Patent
Shick

(10) Patent No.: US 6,228,385 B1
(45) Date of Patent: May 8, 2001

(54) LIQUID ANTIMICROBIAL, SKIN MOISTURIZING FORMULATION

(75) Inventor: Richard Lee Shick, Alpharetta, GA (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 0 days.

(21) Appl. No.: 09/268,393

(22) Filed: Mar. 15, 1999

(51) Int. Cl.$^7$ .......................... A01N 25/26; A01N 25/08; A61K 31/045
(52) U.S. Cl. ..................... 424/419; 424/409; 514/724
(58) Field of Search ..................... 424/81, 401, 405, 424/409, 419; 514/873, 944

(56) References Cited

U.S. PATENT DOCUMENTS

| | | |
|---|---|---|
| 475,413 | 5/1892 | Peterson et al. . |
| 1,728,721 | 9/1929 | Bryson . |
| 3,277,013 | 10/1966 | Gianladis ............................ 252/153 |
| 3,541,581 | 11/1970 | Monson ................................. 252/90 |
| 3,892,853 | 7/1975 | Cobble ................................. 424/195 |
| 3,903,410 | 9/1975 | Akrongold et al. .................... 252/91 |
| 4,065,422 | 12/1977 | Lundmark et al. .................. 260/29.6 |
| 4,102,995 | 7/1978 | Hebborn ................................. 424/81 |
| 4,140,656 | 2/1979 | Mast ..................................... 252/545 |
| 4,401,650 * | 8/1983 | Salamone ............................... 424/78 |
| 4,464,293 | 8/1984 | Dobrin ................................. 252/547 |
| 4,491,539 | 1/1985 | Hoskins et al. ...................... 252/541 |
| 4,861,580 | 8/1989 | Janoff et al. .......................... 424/1.1 |
| 4,956,170 | 9/1990 | Lee ....................................... 424/81 |
| 5,114,957 | 5/1992 | Hendler et al. ...................... 514/356 |
| 5,236,710 | 8/1993 | Guerrero et al. ..................... 424/401 |
| 5,244,666 | 9/1993 | Murley ................................. 424/405 |
| 5,259,984 | 11/1993 | Hull .................................. 252/174.17 |
| 5,288,486 | 2/1994 | White ................................. 424/78.08 |
| 5,308,611 | 5/1994 | Thompson ........................ 424/78.07 |
| 5,346,890 | 9/1994 | Hagiwara et al. ...................... 514/27 |
| 5,360,824 | 11/1994 | Barker ................................. 424/680 |
| 5,376,366 | 12/1994 | Petchul et al. .................... 424/78.07 |
| 5,425,954 | 6/1995 | Thompson et al. .................. 424/401 |
| 5,480,633 | 1/1996 | Simion et al. ...................... 424/70.1 |
| 5,508,029 | 4/1996 | Petchul et al. .................... 424/78.07 |
| 5,573,768 | 11/1996 | Afriat et al. ......................... 424/401 |
| 5,597,556 | 1/1997 | Moghe et al. ......................... 424/65 |
| 5,629,006 | 5/1997 | Hoang et al. ........................ 424/405 |
| 5,661,189 | 8/1997 | Grieveson et al. .................. 514/784 |
| 5,674,509 * | 10/1997 | Date et al. .......................... 424/401 |
| 5,686,089 | 11/1997 | Mitra et al. ......................... 424/405 |
| 5,728,662 | 3/1998 | Vlasblom ............................. 510/130 |
| 5,750,579 | 5/1998 | Kamishita et al. ............... 514/772.6 |
| 5,753,246 * | 5/1998 | Peters ................................. 424/414 |
| 5,830,487 * | 11/1998 | Klofta et al. ........................ 424/402 |
| 5,871,760 * | 2/1999 | Doughty et al. .................... 424/401 |

FOREIGN PATENT DOCUMENTS

| | | |
|---|---|---|
| 0061701A2 | 10/1982 | (EP) . |
| 0604848 A2 | 7/1994 | (EP) . |
| 0627223 A1 | 12/1994 | (EP) . |
| 0792635A2 | 9/1997 | (EP) . |
| 2698102 | 11/1992 | (FR) . |
| 91/00087 | 1/1991 | (WO) . |

OTHER PUBLICATIONS

Patent Abstracts of Europe—FR 02668932A, Date: May 15, 1992.
Patent Abstracts of Europe—GB 02167429A, Date: May 29, 1986.
Patent Abstracts of Europe—GB 02271778A, Date: Apr. 27, 1994.
Patent Abstracts of Europe—WO 09318740A1, Date: Sep. 30, 1993.
Patent Abstracts of Europe—EP 00396394A2, Date: Nov. 07, 1990.
Patent Abstracts of Japan—JP 02–3111408, Date: Dec. 27, 1990.
Patent Abstracts of Japan—JP 03–48611, Date: Mar. 01, 1991.
Patent Abstracts of Japan—JP 04–120012, Date: Apr. 21, 1992.
Patent Abstracts of Japan—JP 08–198735, Date: Aug. 06, 1996.
Patent Abstracts of Japan—JP 08–245357, Date: Sep. 24, 1996.
Abstract—JP H08–104619A, Date: Apr. 23, 1996.
Abstract—JP H08–310942A, Date: Nov. 26, 1996.
Counterpart PCT International Search Report mailed Nov. 3, 1999.

* cited by examiner

Primary Examiner—William R. A. Jarvis
Assistant Examiner—Vickie Kim
(74) Attorney, Agent, or Firm—Karl V. Sidor

(57) ABSTRACT

A liquid antimicrobial, skin moisturizing formulation including: 1) an aqueous alcoholic base; 2) a humectant; 3) a delivery material adapted to release an emollient when the formulation is applied to the skin; and 4) an emollient imiscible in the aqueous alcoholic base and contained by the delivery material. The delivery material encapsulates or entraps the emollient for subsequent release. Desirably, the humectant is glycerin and the emollient is an alkyl-substituted polysiloxane polymer.

18 Claims, 7 Drawing Sheets

LIQUID ANTIMICROBIAL, SKIN MOISTURIZING FORMULATION

FIELD OF THE INVENTION

The present invention relates to liquid formulations for personal cleaning that have antimicrobial activity.

BACKGROUND

Alcohol is used to disinfect hands and body surfaces. In various forms, it is increasingly being used as hand antiseptics, both to supplement soap usage, as well as for situations where soap and water are not readily available. Ethanol and propanols exhibit broad spectrum antimicrobial activity and are non-allergenic, fast-acting, miscible in water, and relatively non-toxic.

These alcohols are effective against a wide variety of bacteria (Gram positive and Gram negative), yeast, molds, and viruses. Unfortunately, they are ineffective against bacterial spores, have no residual action, and are drying to the skin. Viscosity increasing agents (e.g., thickeners) are often added to alcohols to prevent runoff and to increase residence time on the skin. While longer residence time tends to enhance antimicrobial action it also tends to magnify certain undesirable side effects. Frequent use of alcohol gels may cause skin irritation and reduce the skin moisture level. This can be a problem for health care professionals, child care providers, food service workers and others who use alcohol gels to disinfect or sanitize their hands. Skin irritation from frequent use of alcohol gels may also be a problem for many persons suffering from temporary or chronic digestive tract disorders.

Some alcohol gel formulations contain skin moisturizers or conditioners. Unfortunately sufficiently high levels of some of these moisturizers and/or conditioners may cause instability in the alcohol gel over time and could cause the gel to lose viscosity. In addition, at sufficiently high levels these moisturizers and/or conditioners may provide unpleasant tactile sensations after application but before being absorbed by the skin. For example, high levels of moisturizers such as glycerin tend to provide an unpleasant tacky sensation until the glycerin is absorbed by the skin.

Thus, there is still a need for a liquid antimicrobial formulation that may be applied to the skin without causing drying and irritation. There is also a need for a liquid antimicrobial formulation that moisturizes skin. A need exists for a liquid antimicrobial formulation that includes an emollient or other component that counteracts or offsets any unpleasant tactile properties of the formulation.

Meeting these needs are important since it is desirable to disinfect and/or sanitize skin while maintaining good skin health with formulations that employ generally inexpensive, and readily available materials.

SUMMARY OF THE INVENTION

The problems described above are addressed by the present invention which provides a liquid antimicrobial, skin moisturizing formulation including: 1) an aqueous alcoholic base; 2) a humectant; 3) a delivery material adapted to release an emollient when the formulation is applied to the skin; and 4) an emollient imiscible in the aqueous alcoholic base and contained by the delivery material. Generally speaking, the delivery material encapsulates or entraps the emollient and then releases the emollient when the formulation is applied to the skin.

The emollient should be imiscible in the humectant as well as the aqueous alcoholic base. It is contemplated that the emollient may have some relatively low level of miscibility with the aqueous alcoholic base and/or humectant, depending on the type of emollients used.

The delivery material may be a particulate material and may be a finely divided material such as a powder-like material that may be readily dispersed in the aqueous alcoholic base. A feature of the invention is that the delivery material holds or contains the emollient and then releases the emollient when the formulation is applied to the skin. In an embodiment of the invention, the delivery material may encapsulate the emollient. For example, the delivery material may be gel capsules, small plastic beads or spheres and/or similar bubble like structures composed of a single or multiple layers that hold or surround the emollient.

In an embodiment of the invention, the delivery material should entrap the emollient. For example, the delivery material may be adsorbent or high surface area particulate materials such as certain starches, talcs, clays, metals, polymeric entrapment materials and the like.

Desirably, the particulate delivery material is a polymeric entrapment material formed from a variety of polymers such as, for example, polyolefins, nylons, polyacrylics and the like. Exemplary polymeric entrapment materials include one or more materials having the CTFA designation acrylates copolymers. Exemplary acrylates copolymers may be characterized as cross-linked methacrylates appearing as a white, free-flowing powder. Suitable acrylates copolymers may be obtained from Advanced Polymer Systems of Redwood City, Calif., under the trademarks Microspong® and Polytrap®.

Generally speaking, the formulation will contain from about 0.1 to about 5 percent, by weight, of the delivery material containing the emollient. Relatively small amounts of delivery material may be used if it is capable of containing and delivering relatively large amounts of emollient. On the other hand, relatively large amounts of delivery material may be needed if it is capable of containing and delivering relatively small amounts of emollient.

The emollient may be one or more liquid hydrocarbons (e.g., petrolatum), mineral oil and the like, vegetable and animal fats (e.g., lanolin, phospholipids and their derivatives) and/or a silicone materials such as one or more alkyl substituted polysiloxane polymers. More desirably, the emollient is dimethicone or dimethicone and one or more other alkyl substituted polysiloxane polymers.

In some embodiments of the present invention, it is contemplated that liquid hydrocarbon emollients and/or alkyl substituted polysiloxane polymers may be blended or combined with one or more fatty acid ester emollients derived from fatty acids or fatty alcohols.

According to an aspect of the present invention, the emollient reduces the undesirable tactile attributes of the formulation that may be caused by the humectant component. For example, a dimethicone emollient will reduce the level of tacky or sticky sensation that may be caused by the glycerin humectant in the formulation. It is contemplated that the delivery material may also help reduce undesirable tactile attributes of the formulation that may be caused by the humectant component.

While the loading of the emollient in the particulate delivery material will vary depending on the maximum liquid load for the particulate delivery material, particulate delivery materials may contain from about 10 to about 80 weight percent, based on the weight of the particulate delivery material, of the emollient. This level may be at the lower end of the range for starches and talcs and may be at the upper end of the range for acrylates copolymers. For example, when certain agglomerated acrylates copolymers are used, they may be loaded with from about 30 to about 75 weight percent, based on the weight of the particulate delivery material, of an emollient. As another example, the particulate delivery material may contain about 50 to about 70 weight percent, based on the weight of the particulate delivery material, of an emollient.

The humectant may be a water soluble polyhydric alcohol having from 2 to 3 hydroxyl groups and blends thereof. Desirably, the humectant is glycerin.

The amount of humectant in the formulation may vary depending on the level of moisturizing desired. Desirably, the level of humectant may range from about 1 to about 15 percent, by weight. For example, the formulation may contain from about 1 to about 5 percent, by weight, of the humectant (e.g., glycerin). As another example, the formulation may contain from about 4 percent, by weight, of the humectant (e.g., glycerin).

The aqueous alcoholic base contains water and an alcohol component. Generally speaking, the alcohol component may be selected from methanol, ethanol, propanol, isopropanol, butanol, t-butanol, 2-butanol, pentanol, hexanol, and mixtures of these alcohols. In an aspect of the invention, the alcoholic base may contain from about 20 to about 90 percent, by weight of the alcohol component and from about 1 to about 80 percent, by weight, water.

It is contemplated that other materials may be added to the aqueous alcoholic base. For example, the base may further include disinfectants, antiseptics, surfactants, aqueous-alcohol miscible emollients, preservatives, viscosity modifiers, thickeners, colorants, fragrances, and/or buffers and/or pH control agents.

In an aspect of the invention, it is desirable that the liquid antimicrobial, skin moisturizing formulation be in the form of a gel or material having a gel-like or thickened consistency. Desirably, the formulation will have a viscosity in the range of from about 2,000 to about 100,000 centipoise. More desirably, the formulation will have a viscosity in the range of from about 10,000 to about 60,000 centipoise. Even more desirably, the formulation will have a viscosity in the range of from about 15,000 to about 40,000 centipoise. The viscosity may be adjusted so the formulation may be dispensed from any variety of conventional dispensers for such gel-like or thickened materials. Of course, the formulation may be in the form of a low viscosity free-flowing liquid such as, for example, a liquid that could be dispensed from sprayers or spray bottles (e.g., piston-pump type sprayers), squeeze bottles, sponge bottles or similar applicators.

The present invention also encompasses a wet wipe impregnated with a liquid antimicrobial, skin moisturizing formulation of the type described above. The wet wipe substrate is a permeable sheet such as, for example, a nonwoven fabric, woven fabric, knit fabric and combinations thereof. The nonwoven fabric may be a spunbonded web, a web of meltblown fibers, a bonded carded web, a hydraulically entangled web or the like. If the nonwoven fabric contains meltblown fibers, the meltblown fibers may be or may include meltblown microfibers.

The present invention also encompasses a method of moisturizing and/or disinfecting the skin by applying a liquid antimicrobial, skin moisturizing formulation of the type described above. The method may include the step of applying the formulation utilizing a wet wipe impregnated with the formulation.

DETAILED DESCRIPTION

Figure 1:
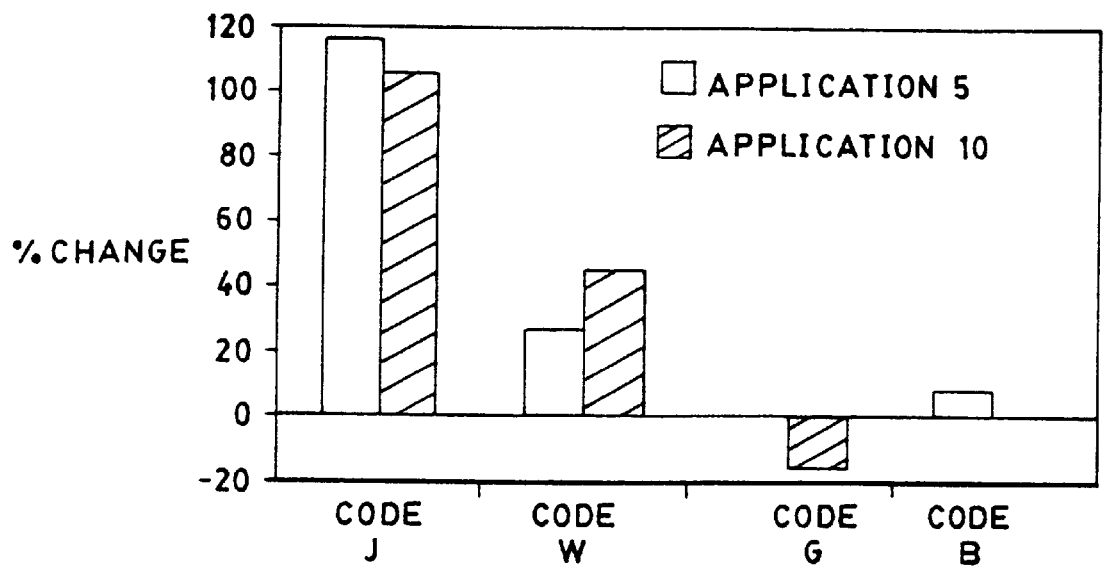
FIG. 1 is a bar graph showing exemplary skin conductance test results.

As used herein, the term "emollient" refers to a liquid that soften or soothe the skin. Emollient are generally hydrophobic materials including, but not limited to silicones and alkyl substituted polysiloxane polymers, petrolatum, mineral oils, animal and vegetable oils and fats, fatty acid esters derived from fatty acids or fatty alcohols, mixtures of hydrocarbon materials that resemble petrolatum in appearance and consistency. Some emollients may be skin protectants as defined by the FDA Skin Protectant monograph. Examples of emollients in this category include dimethicone and petrolatum.

As used herein, the term "skin moisturizing" refers to the action of a material which provides a relatively sustained increase in the level of skin hydration after one or more applications. Such relatively sustained increase in skin hydration may be for a period of up to several hours. The level of skin hydration may be determined by measuring skin conductance utilizing, for example, a Skicon-200 Conductance Meter.

As used herein, the term, "antimicrobial" refers to a substance that kills or inhibits the growth of microorganisms. Exemplary antimicrobial materials include alcohols having from one to about 6 or 7 carbon atoms per molecule. Alcohols exhibit antimicrobial properties when used at sufficiently high concentrations and/or with viscosity increasing agents (e.g., thickeners) to increase the residence time of the alcohol on the skin or on a surface where the alcohol is delivered.

As used herein, the term "particulate" refers to a small, discrete, grain-like portion of material. Examples of particulates include, but are not limited to powders, dusts, grains and the like. The term also encompasses agglomerations of particulates as well as small beads, capsules or other materials.

As used herein, the term "delivery material" refers to a substance that encapsulates or entraps a liquid until it is ready for use and then releases at least a portion of the liquid at once or over a desired period of time. Delivery materials that encapsulate include, for example, capsules, hollow beads, hollow shells, spheres and the like having one or more layers that surround a core of liquid. When the shell or exterior wall(s) of the delivery material is broken, the liquid is dispersed. Delivery materials that entrap include, for example, talcs, starches, clays, and polymeric entrapment materials. Generally speaking, such delivery materials adsorb and hold liquid in a network of voids and interstices. The liquid is thought to be released utilizing one or more of the following mechanisms: wicking, migration, evaporation, mechanical disruption of the delivery material, and displacement. It is contemplated that various combinations of delivery materials may be used together in the formulations of the present invention. It is also contemplated that the same or different delivery materials may be used to encapsulate or entrap the same or different emollients and that such delivery materials may be used in the formulations of the present invention. For example, a first delivery material may contain a first emollient and a second delivery material containing a second emollient may each be added to a formulation.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding, wet-forming and various bonded carded web processes.

As used herein, the term "spunbonded web" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly dispersed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved Device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, the term "microfibers" means small diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881, entitled "A Nonwoven Web With Improved Barrier Properties".

As used herein, the term "sheet" refers to a material that can be a woven fabric, knit fabric, nonwoven fabric or combination thereof.

The present invention encompasses an liquid antimicrobial, skin moisturizing formulation. The formulation includes at least the following components: 1) an aqueous alcoholic base; 2) a humectant; 3) a particulate delivery material adapted to release an emollient when the formulation is applied to the skin; and 4) an emollient imiscible in the aqueous alcoholic base and contained by the particulate delivery material.

Generally speaking, the emollient is a hydrophobic liquid that is imiscible in the aqueous alcoholic base. The emollient is generally also imiscible in the humectant component of the formulation. It is contemplated that the emollient may have some relatively low level of miscibility with the aqueous alcoholic base and/or humectant, depending on the type of emollient used. For example, alkyl substituted polysiloxane polymers and/or petrolatum may be imiscible in the aqueous alcoholic base while fatty acid ester emollients may have some relatively low level of miscibility but would still be generally regarded as imiscible.

Using an emollient that is imiscible in the aqueous alcoholic base is advantageous when the emollient is entrapped or adsorbed in the delivery material. Generally speaking, if the surface energy of the emollient is similar to that of the delivery material and is lower than the surface energy of the aqueous alcoholic base, the emollient will tend to stay entrapped in the delivery material until the formulation is applied to the skin.

The emollient may be one ore more alkyl substituted polysiloxane polymers (e.g., silicones), one or more liquid hydrocarbon emollients such as petrolatum and mineral oils of the type known in the art for use in cosmetic compositions. "Petrolatum" also includes mixtures of hydrocarbon materials which resemble petrolatum in appearance and consistency such as a mixture formed by melting substances such as paraffin wax or microcrystalline wax and the like with mineral oil. The emollient may be selected from vegetable and animal fats (e.g., lanolin, phospholipids and their derivatives. Desirably, the emollient is one or more alkyl substituted polysiloxane polymers. More desirably, the emollient is dimethicone or combinations of dimethicone and other alkyl substituted polysiloxane polymers. These dimethicone and polysiloxane materials will desirably have a viscosity in the range of 20 to 350 centipoise.

If the emollient is one or more alkyl substituted polysiloxane polymers, it is contemplated that it may be blended or combined with one or more fatty acid ester emollients derived from fatty acids or fatty alcohols having from about 12 to 22 carbon atoms. Examples of such esters are methyl, isopropyl and butyl esters of fatty acids such as isopropyl palmitate, isopropyl myristate, isopropyl isostearate, isostearyl isostearate, diisopropyl sebacate, and propylene glycol dipelargonate, as well as 2-ethylhexyl isononoate, 2-ethylhexyl stearate, $C_{12}$–$C_{16}$ fatty alcohol lactates such as cetyl lactate and lauryl lactate, isopropyl lanolate, 2-ethylhexyl salicylate, oleyl myristate, oleyl stearate, oleyl oleate, hexyl laurate, isohexyl laurate and mixtures of the same.

The particulate delivery material may be a finely divided material such as a powder-like material. The size of the particulates may vary from less than 1 micrometer (1 micron or 1 $\mu$m) to about 1000 micrometers or about millimeter. Desirably, the delivery material will have a size ranging from about 5 to a few hundred micrometers. It is also desirable that the delivery material be readily dispersed in the aqueous alcoholic base. This may be accomplished by using particulate delivery materials having a relatively small size. It may also helpful to add viscosity modifiers or thickening agents to the aqueous alcoholic base to help reduce the tendency of the particulate delivery material to settle out.

A feature of the invention is that the particulate delivery material holds or contains the emollient and then releases the emollient when the formulation is applied to the skin. The release of emollient may occur quickly as in the case of emollient encapsulated in capsules, hollow beads and/or shells. These materials are subject to mechanical disrupted or breakage during application. The release of emollient may be a controlled or sustained release as in the case of emollient entrapped in talc, clay, starches, and/or polymeric delivery materials. Release of emollient from such materials may occur through one or more of the following mechanisms: wicking, migration, evaporation, mechanical disruption of the delivery material, and displacement.

For example, the particulate delivery material may be gel capsules, small plastic beads or spheres and/or similar bubble-like structures composed of a single or multiple layers that hold or surround the emollient. In another embodiment of the invention, the particulate delivery material may entrap the emollient. For example, the particulate delivery material may be adsorbent or high surface area materials such as certain starches, talcs, clays, metals, polymeric entrapment materials and the like.

Desirably, the particulate delivery material is a polymeric entrapment material. These materials may be formed from a variety of polymers such as, for example, polyolefins, nylons, polyacrylics and the like. Exemplary polymeric entrapment materials include one or more materials having the CTFA designation acrylates copolymers. Exemplary acrylates copolymers may be characterized as cross-linked methacrylates appearing as a white, free-flowing powder. Suitable acrylates copolymers may be obtained from Advanced Polymer Systems of Redwood City, California, under the trademarks Microsponge® and Polytrap®. An exemplary material available under the Polytrap® trademark is a highly cross-linked polymethacrylate polymer in the form of an amorphous, free-flowing powder. The material has a powder-like structure. The smallest or primary units are individual particles of about 1 micrometer or less in size. These particles partially fuse to form agglomerates ranging in size from about 20 to 80 micrometers. These agglomerates may be held together by electrostatic forces and mechanical entanglement to form still larger aggregates or agglomerates. Such materials may be used to entrap useful levels of emollients for incorporation in the present formulations and may contain about 35 weight percent, based on the weight of the acrylates copolymer, of entrapped dimethicone. Another exemplary acrylates copolymer product is a Polytrap® 7100 macrobeads material containing about 35 weight percent, based on the weight of the acrylates copolymer, of entrapped dimethicone. This material is a highly cross-linked polymethacrylate copolymer in the form of approximately 200 micrometer spherical particles. These particles are described as being adapted to crumble readily as they are spread across the skin. These macrobead materials may desirably contain other levels (e.g., desirably higher levels) of dimethicone. For example, some materials may contain about 50 to about 75 weight percent, based on the weight of the acrylates copolymer, of entrapped dimethicone. Desirably, some materials may contain about 55 to about 65 weight percent, based on the weight of the acrylates copolymer, of entrapped dimethicone.

An exemplary acrylates copolymer available under the Microsponge® trademark is a highly cross-linked polymethacrylate copolymer in the form of approximately 25 micrometer spherical particles. The material has a reported bulk density of about 0.57 g/cc.

Description of useful particulate delivery materials may be found in, for example, U.S. Pat. No. 4,690,825 for "Method For Delivering An Active Ingredient By Controlled Time Release Utilizing A Novel Delivery Vehicle Which Can Be Prepared By A Process Utilizing The Active Ingredient As A Porogen" issued Sep. 1, 1987; U.S. Pat. No. RE 33,429 for "Lattice-Entrapped Emollient Moisturizer Composition" issued Nov. 6, 1990; and U.S. Pat. No. 5,145,675 for "Two Step Method For Preparation Of Controlled Release Formulations" issued Sep. 8, 1992, the contents of which are incorporated herein by reference.

Particulate delivery materials are also described by Abrutyn, E. S. and Saxena, S. J., "Polymeric Controlled Release Topical Cosmetic Applications", Cosmetics & Toiletries, Vol. 107, No. 8, Pps. 65–70 (August 1992); and Klein, W. L., and DiSapio, A. J., "Acrylates Copolymer: A Technique for Entrapping Cosmetic Additives", HAPPI magazine, Vol. 26, No. 7 (July 1989). Generally speaking, the formulation will contain from about 0.1 to about 5 percent, by weight, of the particulate delivery material containing the emollient. Relatively small amounts of particulate delivery material may be used if it is capable of containing and delivering relatively large amounts of emollient. On the other hand, relatively large amounts of particulate delivery material may be needed if it is capable of containing and delivering relatively small amounts of emollient. As an example, relatively small amounts of acrylates copolymer may be adequate while relatively large amounts of starch or talc may be needed to deliver the same level of emollient.

While the loading of the emollient in the particulate delivery material will vary depending on the maximum liquid load for the particulate delivery material, it is generally thought that particulate delivery materials may contain from about 10 to about 80 weight percent, based on the weight of the particulate delivery material, of the emollient. This level may be at the lower end of the range for starches and talcs and may be at the upper end of the range for acrylates copolymers. For example, when certain agglomerated acrylates copolymers are used, they may be loaded with from about 35 to about 75 weight percent, based on the weight of the particulate delivery material, of the emollient. As another example, the particulate delivery material may contain about 50 to about 70 weight percent, based on the weight of the particulate delivery material, of the emollient.

The level of loading may be influenced by modifying the surface energy of the liquid loaded into the particulate delivery material. For example, some acrylates copolymer delivery materials have a surface energy in the range of 40 to 50 dynes per centimeter. An ingredient with a surface energy generally within that range generally wets the particulate and is adsorbed. If the surface energy of the liquid is much higher, it may be lowered by adding an surfactant.

According to an aspect of the present invention, the emollient reduces the undesirable tactile attributes of the formulation that may be caused by the humectant component. For example, an alkyl substituted polysiloxane polymer emollient such as a dimethicone emollient will reduce the level of tacky or sticky sensation that may be caused by the glycerin humectant in the formulation. Although the inventor should not be held to any particular theory of operation, it is thought that the dimethicone emollient forms a layer at the surface of the glycerin which imparts a smooth or non-tacky feel when touched. The particulate delivery material may also help reduce the undesirable tactile attributes of the formulation that may be caused by the humectant component. For example, a fine, powdery particulate delivery material may help provide a smooth, silky feel. Talc may be useful as a delivery material which helps provide desirable tactile attributes. It is contemplated that talc or similar delivery materials may be blended with other particulate delivery materials such as, for example, acrylates copolymers.

The humectant may be a water soluble polyhydric alcohol having from 2 to 3 hydroxyl groups and blends thereof. Desirably, the humectant is glycerin. The amount of humectant in the formulation may vary depending on the level of moisturizing desired. Desirably, the level of humectant may range from about 1 to about 15 percent, by weight. For example, the formulation may contain from about 1 to about 5 percent, by weight, of the humectant (e.g., glycerin).

The aqueous alcoholic base contains water and an alcohol component. Generally speaking, the alcohol component may be selected from methanol, ethanol, propanol, isopropanol, butanol, t-butanol, 2-butanol, pentanol, hexanol, and mixtures of these alcohols. Desirably, the alcohol component is ethanol. In an aspect of the invention, the alcoholic base may contain from about 20 to about 90 percent, by weight of the alcohol component and from about 1 to about 78.5 percent, by weight, water. In another aspect of the invention, the alcoholic base may contain from about 60 to about 90 percent, by weight of the alcohol component and from about 1 to about 38.5 percent, by weight, water.

It is contemplated that other materials may be added to the aqueous alcoholic base. For example, the base may further include antimicrobials, disinfectants antiseptics, surfactants, aqueous-alcohol miscible emollients, preservatives, viscosity modifiers, thickeners, colorants, fragrances, and/or buffers and/or pH control agents.

An exemplary thickening agent is an addition polymer of acrylic acid cross-linked with an unsaturated polyfunctional agent such as a poly-allyl ether of sucrose is employed. Such polymers are described in U.S. Pat. Nos. 2,798,053 and 3,133,865, have the CTFA (Cosmetic, Toiletry and Fragrance Association) adopted name of "Carbomer" and are commercially available under the tradenames CARBOMER® 934, 940 and 941 from B. F. Goodrich Chemicals Group of Cleveland, Ohio and under the tradenames ACRITAMER 934, 940 and 941 from R.I.T.A. Corporation of Crystal Lake, Ill. These polymers may be used in an amount which is sufficient to obtain a gelled composition of viscosity in the range of 10,000 to 100,000 centipoise (10 to 100 pascal second) at 25° C., and for pump dispenser use, preferably from about 10,000 to 50,000 centipoise (10 to 50 pascal second), and most preferably, from about 10,000 to 20,000 centipoise (10 to 20 pascal second), but not so much as to leave a sticky residue on the skin after the alcohol and water in the composition have evaporated. Typically up to about 2 weight percent of the total composition and desirably, up to about 0.7 weight percent of such a thickener is used.

Other thickeners can be used to improve the gel obtained as well as the skin feel of the composition. For example, from about 0.1 to about 0.5, preferably 0.25, weight per cent of a hydroxypropyl guar gum (propylene glycol ether of guar gum) of higher molecular weight and higher degree of substitution such as JAGUAR HP-79 and HP-120 from Alcolac, Inc. of Baltimore, Md. can be used. Examples of other thickeners include Sepigel 307 (polyacrylamide, c 13–14 isoparaffin and Laurth-7), and KLUCEL® 99-HHF available from the Aqualon Division of Hercules, Inc., Wilmington, Del.

Some thickening agents/thickeners may be affected by the high alcohol content of the formulation. In such case, a stabilizing agent and/or neutralizing agent that is compatible with the formulation may be added. Such stabilizing agents and/or neutralizing agents are known and their selection and use would be within the capability of one having ordinary skill in the art.

The formulation may contain a small amount (e.g., less than about 1 weight percent) of one or more surfactants. Desirably, the surfactant is a nonionic surfactant. Anionic or amphoteric surfactants, including zwitterionic surfactants may be used where appropriate.

Exemplary nonionic surfactants are polyethoxylated fatty alcohols of the formula $R'O(CH_2CH_2O)_xH$ where R' is a hydrocarbon radical of from about 12 to 22 carbon atoms and x has a value of from about 2 to 100 and more preferably, from about 2 to 25. The RO— group in the formula can be derived from fatty alcohols having from about 12 to 22 carbon atoms such as lauryl, myristyl, cetyl, hexadecyl, stearyl, isostearyl, hydroxystearyl, oleyl, ricinoleyl, behenyl, and erucyl alcohols, and 2-octadecanol. An example of such surfactants is ceteth-20 (cetyl ether of polyethylene oxide having an average of about 20 ethylene oxide units). This and other such nonionic surfactants are commercially available under the tradename "BRIJ" from ICI Americas, Inc. of Wilmington, Del.

Other examples of nonionic surfactants are those typically used in cosmetics such as alkyl phenols with 6 to 12 carbon in the alkyl chain condensed with 2 to 25 moles of ethylene oxide; mono- and di-fatty acid esters of ethylene glycol wherein the fatty acid moiety contains from about 12 to 22 carbon atoms; fatty acid monoglycerides wherein the fatty acid moiety contains from about 12 to 22 carbon atoms; fatty acid esters of sorbitol sorbitan, polyoxyethlene sorbitol, and olyoxyethylene sorbitan where the fatty acid moiety contains from about 12 to 22 carbon atoms. Such surfactants are well known and many are commercially available.

Exemplary formulations of some embodiments of the invention are given in Table 1. It should be understood that these formulations describe examples of ingredients and composition ranges and are not to be interpreted as limiting the invention to a particular ingredient or composition.

TABLE 1

Exemplary Formulations

| INGREDIENT | Percent Composition (Broad Range) | Percent Composition (Narrower Range) |
|---|---|---|
| HUMECTANT | | |
| Glycerin | 1.0 to 15.0 | 1.0 to 5.0 |
| PARTICULATE DELIVERY MATERIAL | | |
| Acrylates Copolymers | 0.1 to 5.0 | 1.0 to 2.5 |
| EMOLLIENT % loading in particulate delivery material | | |
| Dimethicone | 10 to 80 | 40 to 70 |
| AQUEOUS ALCOHOLIC BASE | to make up 100% | to make up 100% |
| Water | 1 to 78.5 | 1 to 38.5 |
| Ethanol | 20 to 90 | 60 to 80 |
| OTHER INGREDIENTS | | |
| Carbomer ® 940 | 0.0 to 1.0 | 0.0 to 0.5 |
| Triethanolamine | 0.0 to 1.0 | 0.0 to 0.5 |
| Klucel ® 99-HHF hydroxylpropyl cellulose | 0.0 to 1.0 | 0.0 to 0.5 |
| Fragrance | 0.0 to 1.0 | 0.0 to 0.5 |

The present invention also encompasses a wet wipe impregnated with a liquid antimicrobial, skin moisturizing formulation of the type described above.

The wet wipe substrate is a permeable sheet such as, for example, a nonwoven fabric, woven fabric, knit fabric and combinations thereof. The nonwoven fabric may be a spunbonded web, a web of meltblown fibers, a bonded carded web, a hydraulically entangled web or the like. If the nonwoven fabric contains meltblown fibers, the meltblown fibers may be or may include meltblown microfibers. Suitable wet wipes are disclosed in U.S. Pat. No. 4,904,524, issued Feb. 27, 1990, to Yoh; and U.S. Pat. No. 5,656,361, issued Aug. 12, 1997, to Vogt et al., the contents of which are incorporated herein by reference.

EXAMPLES

Formulation

The following examples describe liquid antimicrobial skin moisturizing formulations. Generally speaking, the ingredients are identified by their chemical name, CTFA name, or in some cases, by their trade names. The ingredients were combined by conventional mixing and/or soap formulating techniques. The Carbomer® 940 thickener was mixed into water until it was completely hydrated. This took approximately 40 minutes. The remaining ingredients, with the exception of triethanolamine, were added to the mixture one at a time and allowed to mix fully. Finally, the mixture was thickened by adding triethanolamine. The specific amounts of ingredients for the Skin Moisturization Evaluation are identified in Table 2.

TABLE 2

| INGREDIENT | Code W |
|---|---|
| Ethyl Alcohol | 60.00 |
| Polytrap ® (35% dimethicone) | 1.50 |
| glycerin | 2.00 |
| Carbomer ® 940 | 0.32 |
| triethanolamine | 0.24 |
| fragrance | 0.40 |
| water | 35.54 |

A series of liquid, antimicrobial skin moisturizing formulations were made utilizing an ethyl alcohol gel base utilizing the same formulating techniques described above. Amounts of ingredients in the ethyl alcohol gel base were similar to those listed in Table 2 except that the Polytrap® material and glycerin were not added. The percent compositions for the ethyl alcohol gel base formulation are shown in Table 3

TABLE 3

| INGREDIENT | Percent Composition |
|---|---|
| Ethyl Alcohol | 65.00 |
| Carbomer ® 940 | 0.32 |
| triethanolamine | 0.24 |
| fragrance | 0.40 |
| water | 34.04 |

Various combinations of humectants and emollient were added to this ethyl alcohol gel base including glycerin and a Polytrap® material containing 35 weight percent dimethicone. The various combinations are described in terms weight percent of ingredients added to the ethyl alcohol gel base. The additional ingredients for each of six test product codes are described in Table 4.

TABLE 4

| Product Code | Description of product |
|---|---|
| Code 123 | Ethyl Alcohol Gel base (see Table 3) |
| Code 335 | Ethyl Alcohol Gel base + 2% Polytrap ® material {dimethicone (35%)} |
| Code 472 | Ethyl Alcohol Gel base + 2% glycerin |
| Code 581 | Ethyl Alcohol Gel base + 2% glycerin + 2% Polytrap ® material {dimethicone (35%)} |

Skin Moisturization Evaluation

It has been shown, most notably by Obata and Tagami [Obata, And Tagami, H. "A rapid in vitro test to assess skin moisturizers.", J. Soc. Cosmet. Chem., 41 235–241 (July/August, 1990)], that the ability of an alternating current to flow through the stratum corneum is an indirect measure of its water content.

Skin conductance was measured with an lBS Skicon-200 Conductance Meter model number 03489 available from I.B.S., Ltd., Shizuuka-Ken, Japan. The conductance meter was equipped with an MT-8C probe from Measurement Technologies of Cincinnati, Ohio. The MT-8C probe has 8 pins evenly spaced in a circle about 16mm in circumference. These pins, of alternating polarities are spaced at about 2 mm. With the MT-8C probe, conductance is measured around a 16 mm ring and wet/dry/electrolyte effects are minimized by an averaging effect around the ring.

The experimental equipment reported measurements of skin conductance in units of milliohms. These measurements represented the AC conductance 5 seconds after placing the spring-loaded probe tip to the sample site (i.e., a marked portion of the forearm). The timing interval is believed to be sufficient for the electronic circuits to stabilize in response to the change in conductance but short enough not to be influenced by increased hydration at the probe tip due to its being occlusive and acting as a hindrance to the normal water loss at the test site.

An experiment was conducted to compare the effects of four alcohol gel products on the stratum corneum overtime with multiple applications. The following alcohol gels were evaluated:

| Product Code | Description of product |
|---|---|
| Code J | Viragel ®, available from Veridien, Inc. |
| Code W | See description in Table 2 |
| Code G | Sanigel ®, available from Central Solutions, Inc. |
| Code B | Purell ® w/aloe, available from GoJo ® Inc. |

Purell® with aloe contains approximately 62% ethyl alcohol, with smaller amounts of isopropyl alcohol, emollients and thickeners. Viragel® contains approximately 70% isopropyl alcohol with smaller amounts of propylene glycol, thickener and fragrance. Sanigel® contains approximately 69% ethyl alcohol 15 and smaller amounts of glycerin, thickener and fragrance.

Four panelists were instructed to avoid using soap or any type of moisturizing products on the forearm area 24 hours prior to their first scheduled session. The subjects acclimated in a controlled room set at 70° F., 40%RH for 30 minutes. Upon acclimation, each subject had two 5 cm by 5 cm test sites outlined on their volar forearm using a standard template A series of baseline measurements were taken from each test site with the Skicon-200 Conductance Meter. Five conductance readings were taken in the 5 cm×5 cm test site and averaged. Five skin hydration readings per second for 2 minutes were taken and averaged. Test product was applied (0.1 mL) to each site in a randomly ordered sequence. The product was applied with a gloved hand using a quarter size circular motion. The time in which it took for the product to dry on the forearm was recorded. After the product dried, skin conductance measurements were taken at 1 minute and 10 minutes and then at 30 and 60 minutes The product was reapplied to the skin every 30 minutes, three times. During each session two products were evaluated. The testing was carried out for four consecutive days.

The results depicted in FIG. 1 shows that the average 5 and 10 application conductance measurements taken 10 minutes after the last application on day 1 are lower than baseline for Code G (Sanigel®), slightly higher for B (Purell® w/aloe), but are much higher for Codes J (Viragel®) and W (New Formulation). This appears to indicate that Codes J and W increase skin moisture and Codes G and B do not increase skin moisture.

Figure 2:
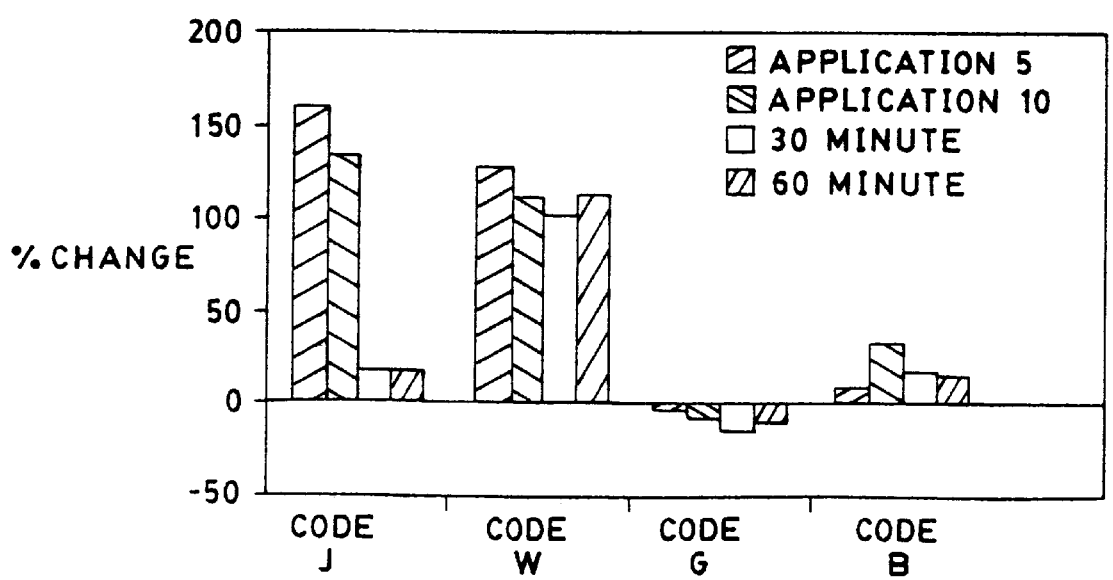
FIG. 2 is a bar graph showing exemplary skin conductance test results.
Figure 3:
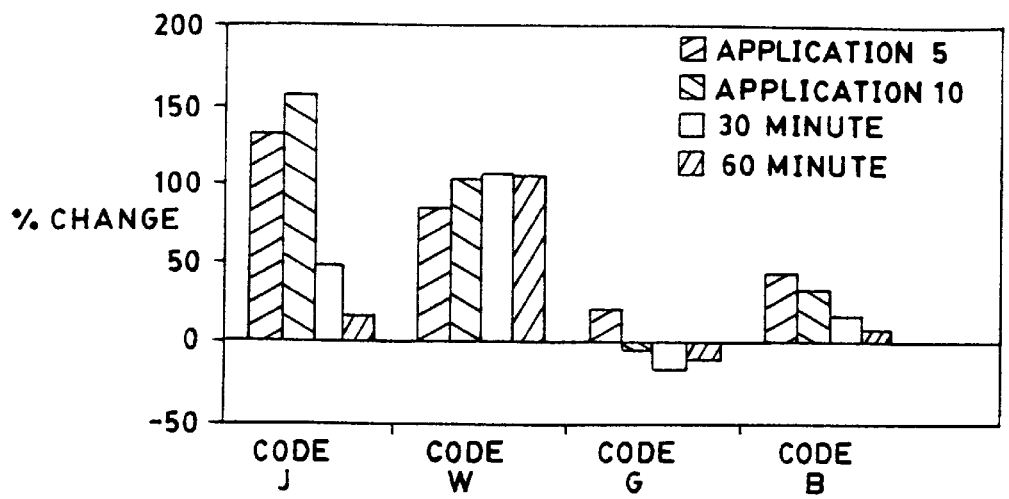
FIG. 3 is a bar graph showing exemplary skin conductance test results.

The results depicted in FIGS. 2 and 3 show that the average 30 and 60 minute conductance measurement taken after the $10^{th}$ application on days 2 and 3 are lower than baseline for Code G and slightly higher for Code B and Code J. Code W is higher than baseline. Code W increases skin moisture for at least 60 minutes after the $10^{th}$ application whereas Code J decreases significantly over this time frame. This appears to indicate that the glycerin in the formula is being retained in the skin which increases skin moisture.

Figure 4:
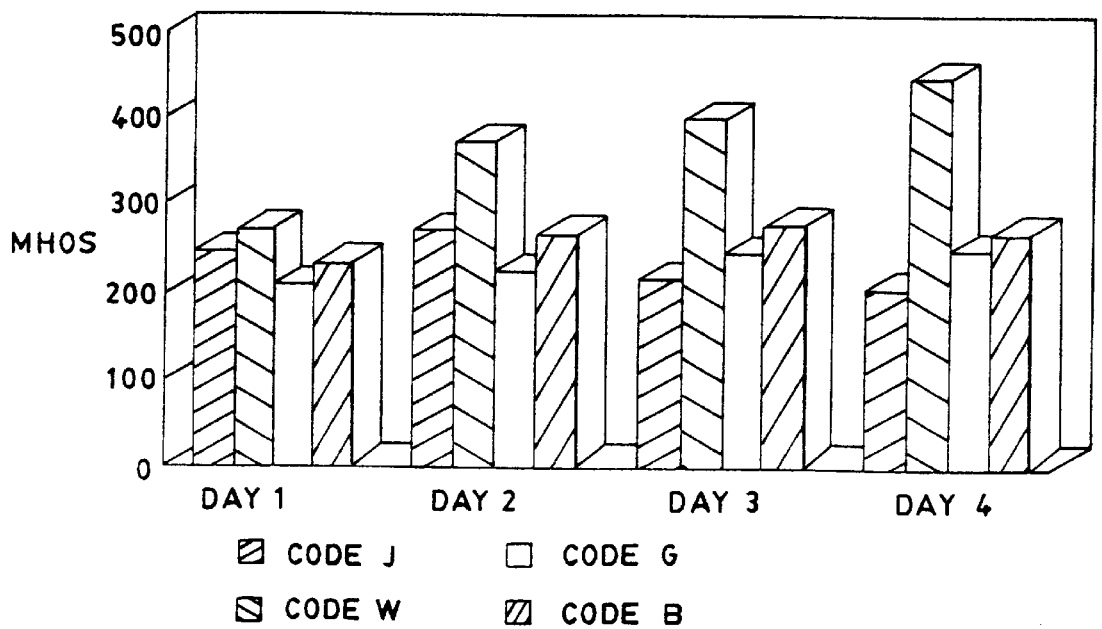
FIG. 4 is a bar graph showing exemplary skin conductance test results.

FIG. 4 depicts the baseline readings for each code over 4 days. Code W has the highest increase in baseline readings over four days. This appears to indicate that the product maintains moisture over a 24 hour time period. Codes J and C have the lowest baseline readings throughout the study. Code J (viragel®) has fairly low baseline readings from day to day. However, SkiCon measurements indicate that the product appears to increase skin conductance shortly after application. This would mean that the skin loses this moisture overnight. Code G's (Sanigel®) baseline measurements do not vary much from day to day.

The skin conductance testing was carried out in a separate study for the alcohol gel formulations identified in Table 4. The study utilized the same equipment and test procedures as described above except that there were six panelists.

Figure 5:
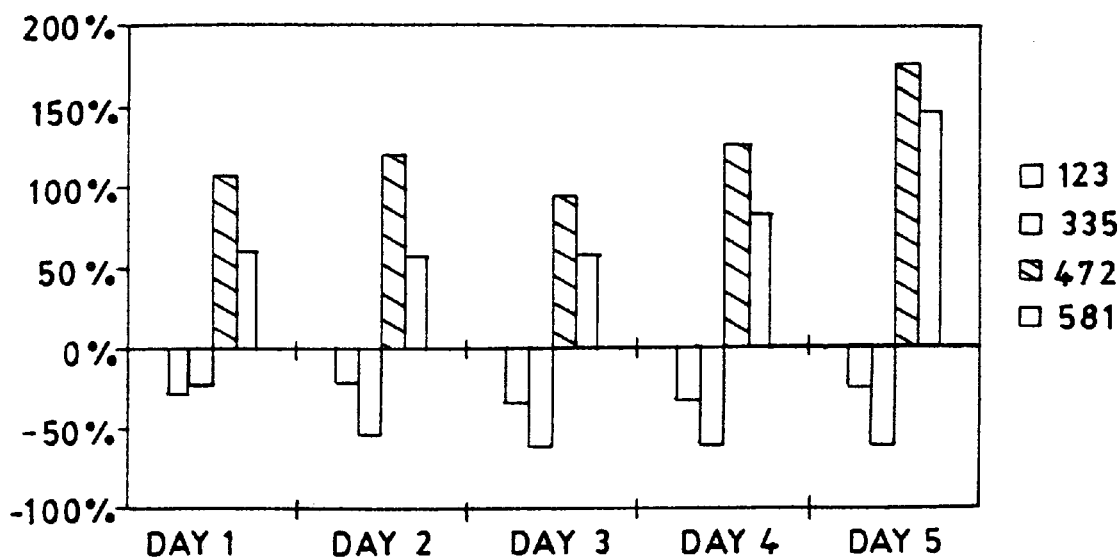
FIG. 5 is a bar graph showing exemplary skin conductance test results.
Figure 6:
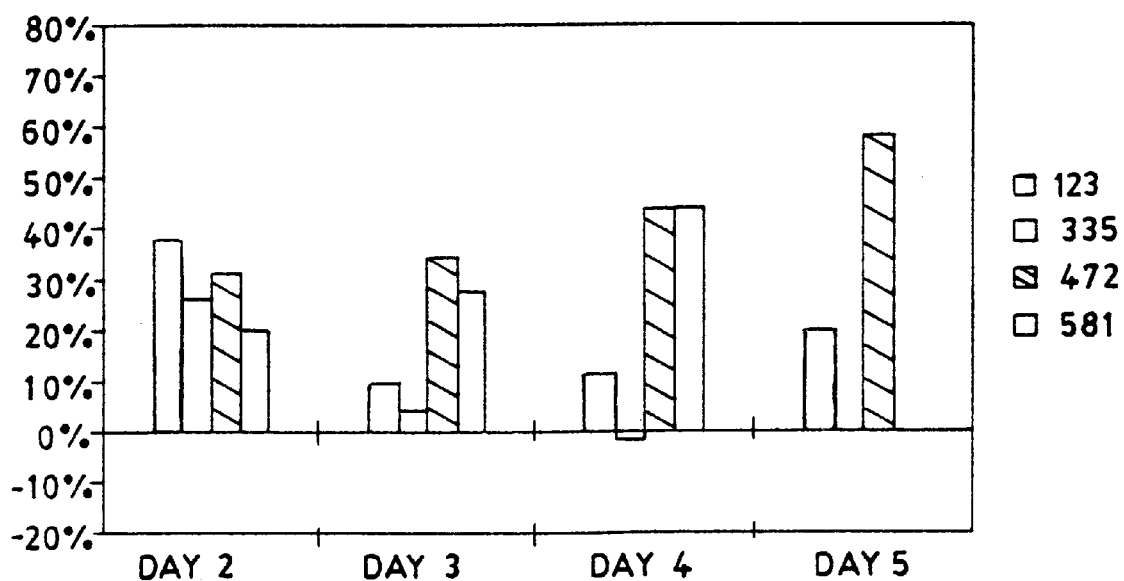
FIG. 6 is a bar graph showing exemplary skin conductance test results.

The results of testing the formulations of Table 4 are reported in FIGS. 5–9. The graphical representation of skin conductance data in FIGS. 5–9 are grouped by day. Within each group are individual bars representing the skin conductance reading for a particular code. The individual bars within each group are arranged in sequence and represent (from left to right): Code 123, Code 335, Code 472, and Code 581. FIGS. 5 and 6 show the percent change from the day 1 baseline over five days. This data indicate that codes 472 and 581 (all containing glycerin) increase skin moisture over time. Although code 581 has the highest change, this may not be significant due to small sample size. The highest increase in moisture occurs on day five. This is thought to be caused by the numerous applications of product on the skin and the accumulation of glycerin in the stratum corneum. Codes 123 and 335 did not increase skin hydration readings over time. This data shows that products containing glycerin increase skin moisture. There appears to be a tendency for formulations containing acrylates copolymers products but not glycerin to dry the skin.

Figure 7:
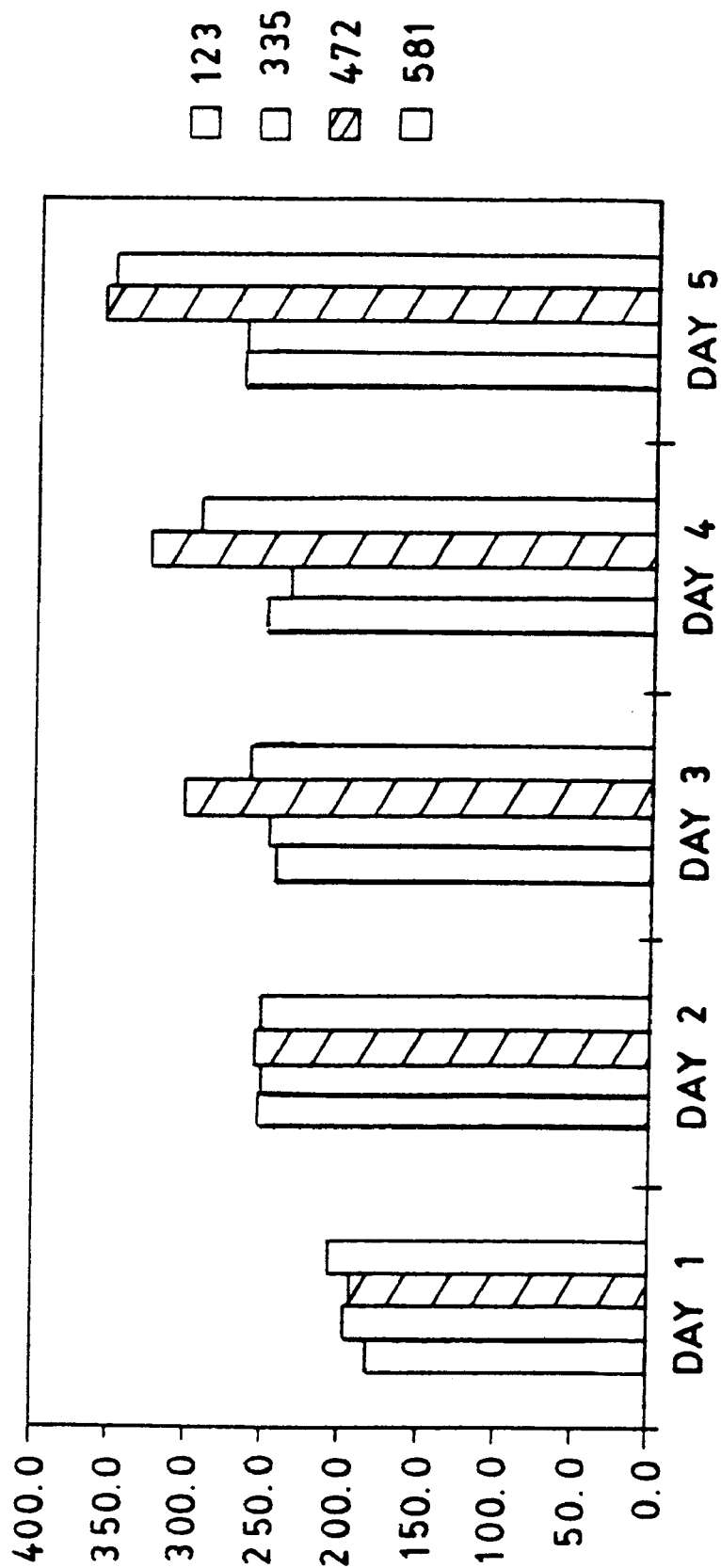
FIG. 7 is a bar graph showing exemplary skin conductance test results.

FIG. 7 depicts the absolute baseline readings over five days. There is a steady increase in skin hydration from day to day for codes 472 and 581. Day five has the highest increase in skin hydration for all six codes.

Figure 8:
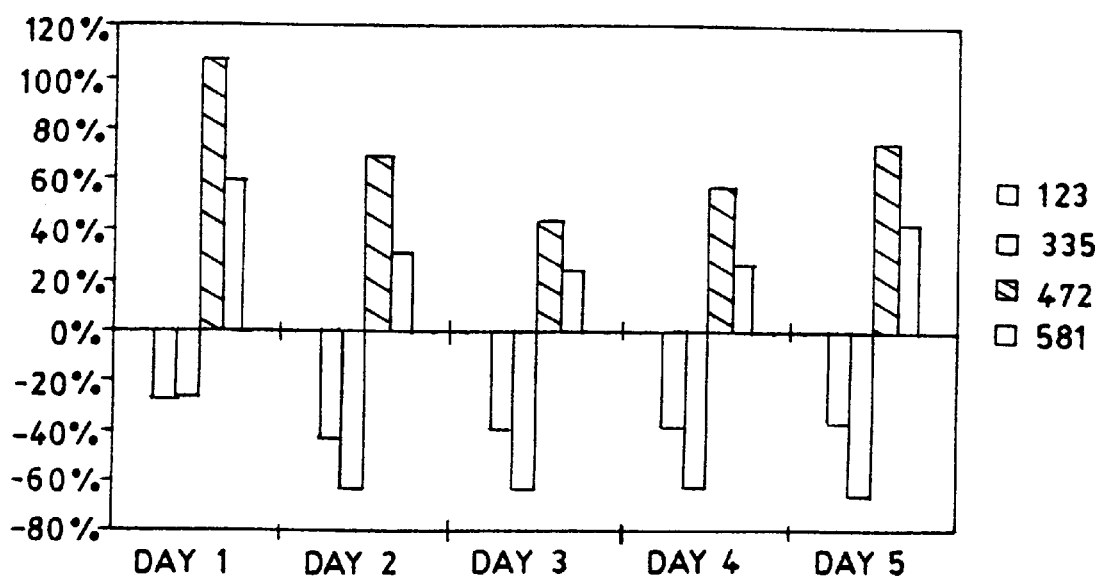
FIGS. 8 and 9 are bar graphs showing exemplary skin conductance test results.
Figure 9:
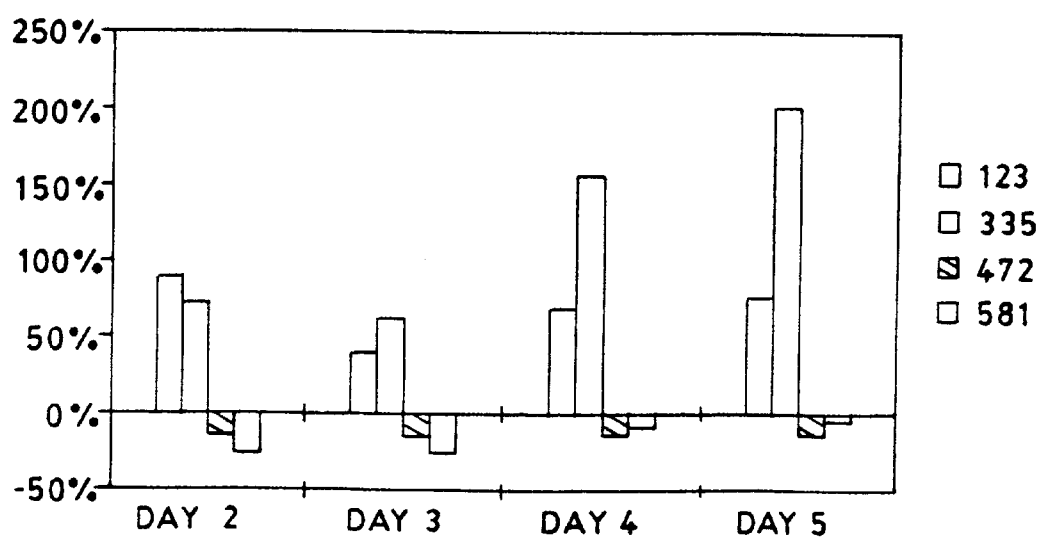

FIG. 8 depicts the change in readings form the morning baseline until thirty minutes after the $10$th application. FIG. 9 depicts the overnight change in readings. Application of glycerin containing formulations increases the skin conductance readings during the day, while alcohol gels without glycerin result in lower readings (corresponding to drier skin). There is also a recovery overnight in the opposite direction. High moisture levels are somewhat lost, while dry skin picks up moisture. For glycerin, the magnitude of recovery creates an overall increase throughout the five days.

There appears to be a greater drop in skin conductance during the day with formulations containing dimethicone emollients. This appears to be an artifact of the test method caused by dimethicone acting as an insulator against the electrical measurement of the skin conductance meter. With normal shedding of skin and dissipation of the dimethicone layer overnight, this apparent insulating effect is lost and baseline readings are consistent.

Tactile Testing—Paired Comparisons

The effects of seven formulations were evaluated in a paired comparison use test. Six formulations differed in glycerin composition and the presence or absence of an emollient ingredient that reduced unpleasant tactile sensations. The specific amounts of ingredients for the Tactile Testing—Paired Comparisons are identified in Table 5.

TABLE 5

| | Percent Composition | | | | | |
|---|---|---|---|---|---|---|
| | Code 781 | Code 525 | Code 245 | Code 337 | Code 123 | Code 473 |
| Ethyl Alcohol | 65.00 | 65.00 | 65.00 | 65.00 | 65.00 | 65.00 |
| Polytrap ® (35% Dimethicone) | 0.00 | 2.00 | 0.00 | 2.00 | 0.00 | 2.00 |
| Carbomer ® 940 | 0.32 | 0.32 | 0.32 | 0.32 | 0.32 | 0.32 |
| triethanolamine | 0.24 | 0.24 | 0.24 | 0.24 | 0.24 | 0.24 |
| fragrance | 0.40 | 0.40 | 0.40 | 0.40 | 0.40 | 0.40 |
| water | 26.04 | 24.04 | 30.04 | 28.04 | 32.04 | 30.04 |
| glycerin | 8.00 | 8.00 | 4.00 | 4.00 | 2.00 | 2.00 |

The Viragel® product utilized in this study contained approximately 70% ethyl alcohol with smaller amounts of propylene glycol, thickener and fragrance. The Viragel® was labeled as Code 684.

The four product comparisons evaluated in this study were as follows:

Comparison 1 Code 781 (2% Glycerin)
    Code 525 (2% Glycerin+emollient)
Comparison 2 Code 245 (4% Glycerin)
    Code 337 (4% Glycerin+emollient)
Comparison 3 Code 123 (8% Glycerin)
    Code 473 (8% Glycerin+emollient)
Comparison 4 Viragel®—Code 684
    Code 337 (4% Glycerin+emollient)

Nineteen panelists participated in this study. They were instructed to wash their hands three times with 1 ml of Triangle Lotion Soap prior to the application of test product. This was done to remove any dirt or impurities that may have been on the skin. A one (1) mL portion of test product was injected onto the palm of each panelist's hand by the study moderator. Panelists were asked to massage the product into the skin until absorbed. Once absorbed, the panelists made an initial tackiness evaluation of their skin. Panelists then waited three minutes and made a final evaluation.

The panelists washed their hands in between evaluations to remove prior product. The comparative hand gel was then injected onto the palm of their hand and the procedure was repeated At this time, the panelists were asked to determine which of the two products felt tackier on their skin and by how much. A ten point rating scale was used to determine the degree of tackiness detected with one (1) being the smallest level of difference and ten (10) being the greatest level of difference. The results from this study are shown in Table 6 and in FIGS. 9 and 10.

TABLE 6

Tactile Testing-Paired Comparisons

|  | 781 | 525 | 245 | 337 | no diff | 123 | 473 | no diff | 684 | 337 | no diff |
|---|---|---|---|---|---|---|---|---|---|---|---|
| Which product feels tackier on your hands? | | | | | | | | | | | |
| Initial Rating | 84% | 16% | 90% | 5% | 5% | 95% | 5% |  | 95% | 5% |  |
| 3 Minute Rating | 95% | 5% | 95% | 5% |  | 90% | 5% | 5% | 84$ | 11% | 5% |
| How much tackier does this product feel? | | | | | | | | | | | |
| Initial Rating | 7 |  | 6 |  |  | 7 |  |  | 6 |  |  |
| 3 Minute Rating | 7 |  | 6 |  |  | 6 |  |  | 5 |  |  |

Rating Scale
1=No difference.
3=Very small difference, not confident, someone could miss it.
5=Slight difference, confident about judgment.
7=Moderate difference, easy to detect, confident.
9=Very large difference, very easy to detect, memorable.

Figure 10:
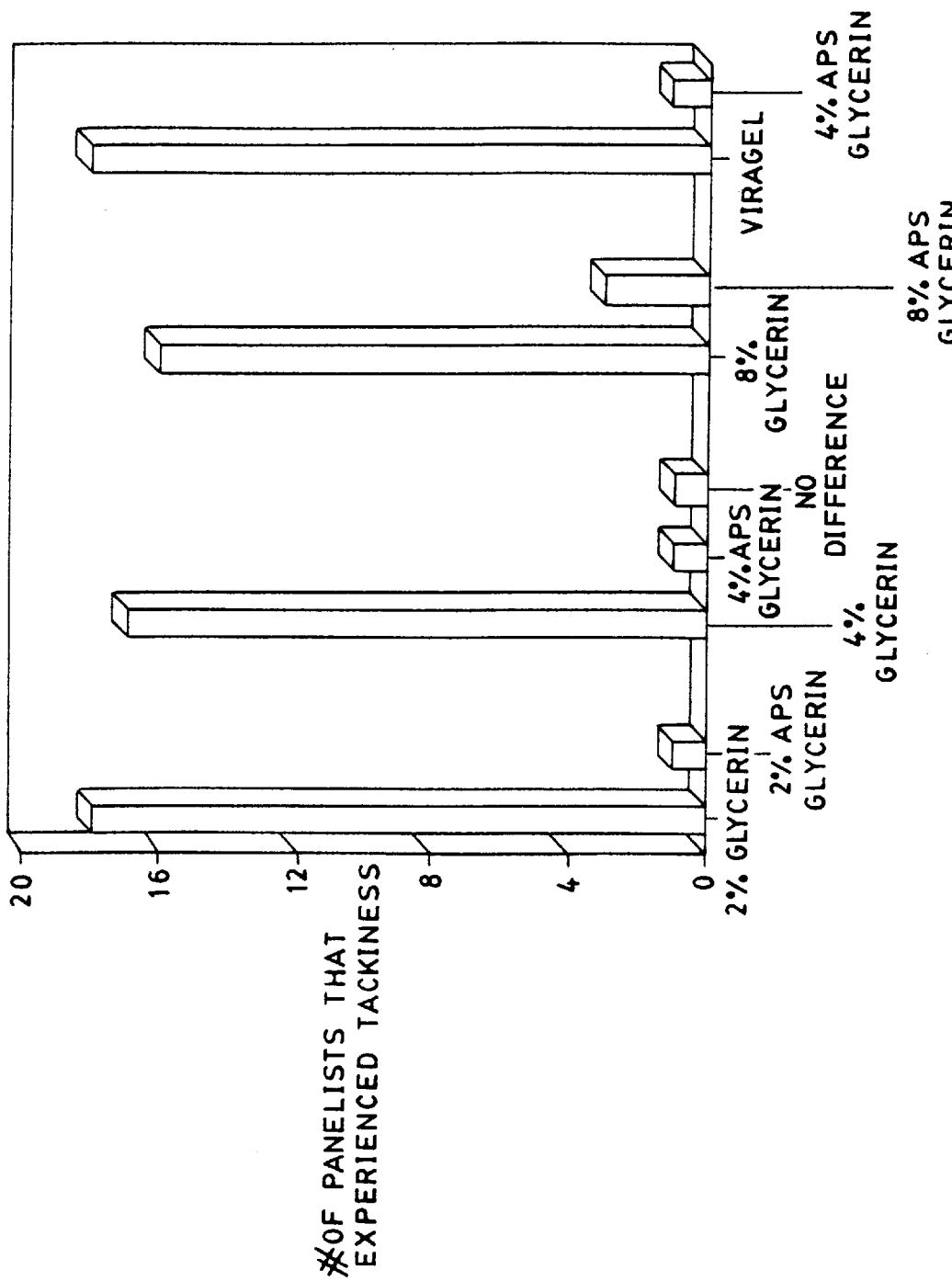
FIG. 10 is a bar graph showing exemplary paired comparison tactile test results.
Figure 11:
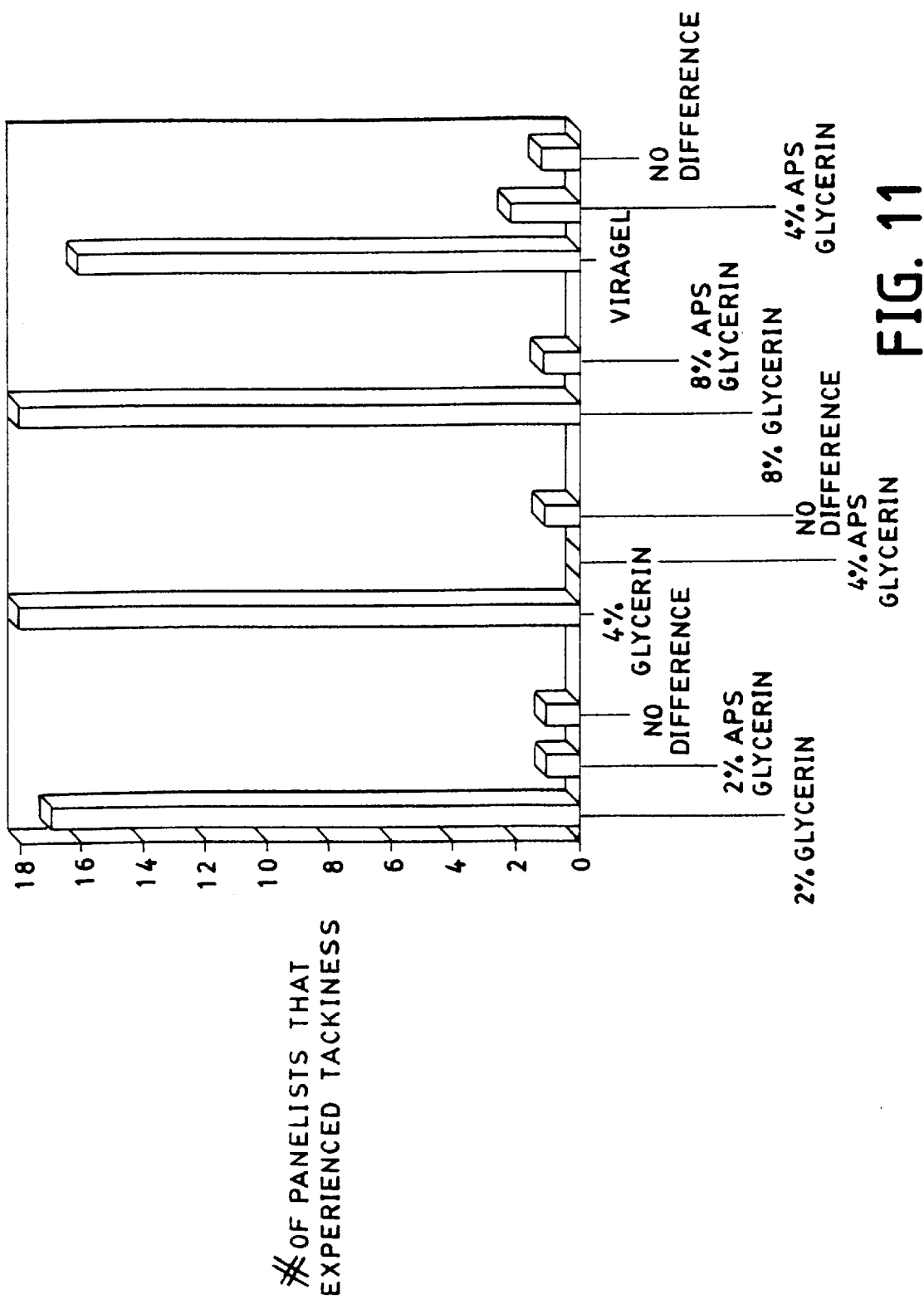
FIG. 11 is a bar graph showing exemplary paired comparison tactile test results.

FIG. 9 shows the initial rating of the panelists. FIG. 10 shows the rating of the panelists after 3 minutes. In FIGS. 9 and 10, it should be noted that the products containing the emollient entrapped in the particulate delivery material were labeled with a percentage level of glycerin followed by the term "APS Glycerin".

Tactile Testing—After Feel

A test was conducted to evaluate the tackiness of two of the product codes described above to determine the effect of the emollient. The product codes tested both contained 4& glycerin. Code 245 lacked an emollient. Code 337 contained 2% of Polytrap® acrylates copolymers loaded with 35 weight percent, based on the weight of the Polytrap® material of dimethicone emollient.

Six panelists participated in this study. They followed the following test procedure:

1. The panelists were instructed to wash their hands with 1 ml of Triangle™ lotion soap (available from Kimberly-Clark Corporation) prior to the application of test product.
2. 1 ml of test product was injected onto the palm of the panelist's hand.
3. While still wet, the panelists generated a list of attributes describing the initial feel of the test product.
4. Once the product absorbed into the skin, the panelists generated a list of attributes describing the after feel of the test product.
5. The panelists timed and recorded how long the product remained tacky.
6. The procedure was repeated using the second test product. The products were random sorted to reduce variability.

An average period of time during which tackiness was perceived was reported for each code.
Code 337 (Glycerin+Dimethicone)=1 minute of tackiness.
Code 245 (Glycerin)=19 minutes of tackiness.
Code 337—Attributes
  Initial Feel (while wet)—cool, gritty, pasty, smooth, slimy.
  After Feel (while dry)—cool, moisturized, smooth, silky, powdery.
Code 245—Attributes
  Initial Feel (while wet)—cool, sticky, pasty, smooth, slimy.
  After Feel (while dry)—cool, moisturized but still sticky, tacky, gummy, pasty, slimy, gluey.

While the present invention has been described in connection with certain embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A liquid antimicrobial, skin moisturizing formulation comprising:
  an aqueous alcoholic base comprising at least 20 percent, by weight, alcohol;
  a humectant;
  a particulate delivery material selected from polymeric entrapment materials identified as acrylates copolymers, the particulate delivery material being adapted to entrap an emollient and further adapted to release an emollient when the formulation is applied to the skin; and
  an emollient imiscible in the aqueous alcoholic base and entrapped by the particulate delivery material.

2. The formulation of claim 1, wherein the emollient is imiscible in the humectant.

3. The formulation of claim 1, wherein the emollient is selected from alkyl substituted polysiloxane polymers and mixtures thereof.

4. The formulation of claim 1, wherein the emollient is selected from polydimethylsiloxane polymers and mixtures thereof.

5. The formulation of claim 1, wherein the delivery material contains from about 10 to about 80 percent, by weight, of an emollient.

6. The formulation of claim 1, wherein the delivery material contains from about 50 to about 75 percent, by weight, of an emollient.

7. The formulation of claim 1, wherein the delivery material contains from about 50 to about 70 percent, by weight, of an emollient.

8. The formulation of claim 1, wherein the humectant is selected from water soluble polyhydric alcohols having from 2 to 3 hydroxyl groups.

9. The formulation of claim 1, wherein the humectant is selected from glycerin, propylene glycol, dipropylene glycol, polyethylene glycol, butylene glycol, hexane triol and mixtures thereof.

10. The formulation of claim 1, wherein the aqueous alcoholic base comprises water and an alcohol component selected from methanol, ethanol, propanol, isopropanol, butanol, t-butanol, 2-butanol, pentanol, hexanol, and mixtures thereof.

11. The formulation of claim 1, wherein the aqueous alcoholic base comprises a gel.

12. The formulation of claim 1, wherein the emollient forms a coating over the humectant when the formulation is applied to the skin.

13. A liquid antimicrobial, skin moisturizing formulation comprising;

an alcoholic base comprising from about 60 to about 90 percent, by weight of an alcohol and from about 1 to about 38.5 percent, by weight, water;

from about 1 to about 10 percent, by weight, of a humectant; and from about 0.5 to about 6 percent, by weight, of a particulate delivery material selected from polymeric entrapment materials identified as acrylates copolymers, the particulate delivery material being adapted to entrap an emollient and further adapted to release an emollient, imiscible with the aqueous alcoholic base, when the formulation is applied to the skin, the particulate delivery material containing from about 10 to about 80 weight percent, based on the weight of the particulate delivery material, of the emollient.

14. The formulation of claim 13, wherein the alcohol is selected from methanol, ethanol, propanol, isopropanol, butanol, t-butanol, 2-butanol, pentanol, hexanol, and mixtures of these alcohols.

15. The formulation of claim 13, wherein the humectant is selected from water soluble polyhydric alcohols having from 2 to 3 hydroxyl groups.

16. A liquid antimicrobial, skin moisturizing formulation comprising:

an alcoholic base comprising from about 60 to about 90 percent, by weight of an alcohol selected from methanol, ethanol, propanol, isopropanol, butanol, t-butanol, 2-butanol, pentanol, hexanol, and mixtures thereof, and from about 1 to about 38.5 percent, by weight, water;

from about 1 to about 10 percent, by weight, of a humectant selected from water soluble polyhydric alcohols having from 2 to 3 hydroxyl groups; and from about 0.5 to about 5 percent, by weight, of an acrylates copolymer particulate delivery material, the particulate delivery material being adapted to entrap an emollient and further adapted to adapted to release an emollient, imiscible with the aqueous alcoholic base, when the formulation is applied to the skin, the particulate delivery material containing from about 10 to about 80 weight percent, based on the weight of the particulate delivery material, of an emollient selected from alkyl substituted polysiloxane polymers and mixtures thereof.

17. A wet wipe comprising:

a porous sheet adapted to contain and release a liquid; and a liquid antimicrobial, skin moisturizing formulation comprising:

an aqueous alcoholic base comprising at least 20 percent, by weight, alcohol;

a humectant;

a particulate delivery material, the particulate delivery material being selected from polymeric entrapment materials identified as acrylates copolymers and adapted to entrap an emollient and further adapted to adapted to release an emollient when the formulation is applied to the skin; and an emollient imiscible in the aqueous alcoholic base and entrapped by the particulate delivery material.

18. A method of disinfecting and moisturizing skin comprising:

applying a liquid antimicrobial, skin moisturizing formulation comprising;

an aqueous alcoholic base comprising at least 20 percent, by weight, alcohol;

a humectant;

a particulate delivery material, the particulate delivery material being selected from polymeric entrapment materials identified as acrylates copolymers and adapted to entrap an emollient and further adapted to adapted to release an emollient when the formulation is applied to the skin; and an emollient imiscible in the aqueous alcoholic base and entrapped by the particulate delivery material.

* * * * *